United States Patent [19]

DiLeo et al.

[11] Patent Number: 5,457,986
[45] Date of Patent: Oct. 17, 1995

[54] PROCESS FOR EVALUATING SOLUTE RETENTION CHARACTERISTICS OF MEMBRANES

[75] Inventors: Anthony J. DiLeo, Westford; Michael W. Phillips, Burlington, both of Mass.

[73] Assignee: Millipore Corporation, Bedford, Mass.

[21] Appl. No.: 189,395

[22] Filed: Jan. 28, 1994

Related U.S. Application Data

[63] Continuation-in-part of Ser. No. 906,730, Jun. 30, 1992, Pat. No. 5,282,380.

[51] Int. Cl.$^6$ .................................................. G01N 15/08
[52] U.S. Cl. ............................................ 73/38; 73/64.55
[58] Field of Search ...................................... 73/38, 64.55

[56] References Cited

U.S. PATENT DOCUMENTS

| | | | |
|---|---|---|---|
| 4,701,861 | 10/1987 | Kauke | 73/38 X |
| 4,872,974 | 10/1989 | Hirayama et al. | 73/38 X |
| 4,881,176 | 11/1989 | Kononov | 73/38 X |
| 5,064,529 | 11/1991 | Hirayama et al. | 73/38 X |

FOREIGN PATENT DOCUMENTS

| | | | |
|---|---|---|---|
| 3312729 | 10/1984 | Germany | 73/38 |
| 142445 | 5/1992 | Japan | 73/38 |
| 1679295 | 9/1991 | U.S.S.R. | 73/38 |

*Primary Examiner*—Thomas P. Noland
*Assistant Examiner*—J. David Wiggins
*Attorney, Agent, or Firm*—Andrew T. Karnakis; Paul J. Cook

[57] ABSTRACT

A process is provided for rapidly and non-destructively evaluating the solute retention characteristics of porous membranes using a novel liquid-porosimetric technique. A ratio of two membrane permeabilities is measured at preselected operating conditions using a pair of mutually immiscible fluids, one of which is employed as a membrane wetting agent and the other used as an intrusion fluid. At the first operating condition, a particular transmembrane pressure is chosen so as to intrude nearly all of the pores present in the membrane sample. At the second operating condition, a particular membrane permeability is chosen so as to achieve a specified permeability ratio. The resulting transmembrane pressure corresponding to this particular membrane permeability is compared to a previously established standard curve which permits identifying the solute retention characteristics of the porous membrane.

28 Claims, 4 Drawing Sheets

PROCESS FOR EVALUATING SOLUTE RETENTION CHARACTERISTICS OF MEMBRANES

REFERENCE TO RELATED APPLICATION

This application is a continuation-in-part of application Ser. No. 07/906,730, filed Jun. 30, 1992 now U.S. Pat. No. 5,282,380.

BACKGROUND OF THE INVENTION

This invention relates to a process for non-destructively evaluating the integrity and intrinsic performance characteristics of porous membranes such as ultrafiltration membranes. More particularly, this invention relates to a non-destructive testing process the quantitatively determining the effect of undesirable large pores in a membrane which, when present, drastically degrade the membrane's solute retention capabilities.

Ultrafiltration membranes have pores of a size typically between about 10 Angstroms and 0.05 microns. It is widely believed that the majority of pores present in ultrafiltration (UF) membranes (~80%) lie within a narrow range of the pore distribution. However, since the membrane permeability, and consequently, the transmembrane transport depend upon the fourth power of the pore radius, these smaller pores usually contribute less than 10% to the total membrane permeability. As a consequence, a very small number of large-sized pores actually control the membrane performance. For membranes whose retention of solute molecules is based upon a sieving mechanism, the evaluation of the "active" pore size distribution is of cardinal importance in predicting the selective transport through such membranes. Therefore, to accurately correlate solute retention, it is necessary to characterize these larger "transport controlling" pores.

The bubble point test and the air diffusion tests are two non-destructive integrity tests which have been previously employed in an attempt to correlate and predict solute retention for various classes of membranes. In the bubble point test, a thoroughly wetted membrane is placed into a housing and contacted with air. The upstream air pressure is then gradually increased, eventually resulting in the selective intrusion of air through the largest pores and the subsequent formation of air bubbles downstream of the membrane. Assuming cylindrical pores, the pore diameter corresponding to the pressure at which these bubbles are first observed (bubble point) can be approximated by the modified Young-Laplace capillary equation given by $$P = \frac{4K\gamma\cos\theta}{d_p} \quad (1)$$

where P is the transpore pressure drop, $d_p$ is the pore diameter intruded, $\theta$ is the contact angle, K represents a shape correction factor, and $\gamma$ is the air-liquid interfacial tension. Since capillary forces dictate that the largest pores are those first intruded with air, the bubble point test can be considered a measure of the largest pore present in the given membrane sample. It is the characterization and quantification of these largest pores which is essential for developing a test capable of correlating and predicting solute retention. However, two problems exist with the traditional bubble point test as it pertains to the evaluation of ultrafiltration membranes. First, due to the extremely large interfacial surface tension at the air/liquid interface, the pressures required to observe the bubble point for typical ultrafiltration (UF) membranes are in excess of 500 psi. Conventional UF membranes may compress when subjected to pressures in this range, leading to results that could be incorrectly interpreted. Second, as the membrane area to be tested increases, the actual membrane bubble point becomes more difficult to detect due to the large background of air diffusing through the wetted membrane. Although this problem can be minimized by utilizing a gas that has a low solubility in the wetting liquid used to intrude the pores, diffusion due to solubility effects can not be totally eliminated. Consequently, this test is essentially limited to small area microfilters.

In the air diffusion test, the membrane is again wetted and contacted with air. The air pressure is increased to some prescribed value below the membrane's bubble point and the total amount of air flow through the wetted membrane by diffusion and convection is recorded. Since the operating pressure is usually well below the bubble point of the membrane, integral membranes exhibit only diffusional flow. In fact, only gross defects present in the membrane sample, those which contribute measurable convective air flow, can be detected. Thus, on a theoretical basis, this test can not be expected to correlate well to the solute retention of integral membranes since this test has sensitivity only to gross defects.

A permoporometric technique for the characterization and pore size distribution determination of various classes of UF membranes is disclosed by:

"Membrane Morphology and Transport Properties", *Desalination*, 53 11 (1985),

"Computer Driven Porosimeter for Ultrafiltration Membranes", *Characterisation of Porous Solids*, K. K. Unger, et al., eds., 283 (1988), "Permoporometric Study on Ultrafiltration Membranes", *J. Membrane Sci.*, 41 69 (1989), and "Correlation of Direct Porosimetric Data and Performance of Ultrafiltration Membranes", *Proc. Biochem. Int'l.*, 111 (1990).

In this permoporometric technique, the air-liquid interface typically encountered in bubble point testing is now replaced with the interface between two immiscible liquids. The key advantage with utilizing a two phase liquid system is the extremely small interfacial tensions associated with many pairs of immiscible liquids, resulting in low transmembrane pressures necessary to selectively intrude nanometer sized pores. In addition, since the two phases are completely immiscible, there is no background diffusional flow to contend with, resulting in a technique which is linearly scalable and independent of membrane surface area. Thus, this technique is eminently suitable for the characterization of UF membranes.

In the disclosed permoporometric technique, a membrane sample is first wetted with one of two mutually immiscible liquid phases (wetting phase). The other immiscible liquid phase (intrusion phase) is then placed upstream of the membrane housing. The intrusion phase is then sequentially pumped through the membrane sample at prescribed flow rates and the resulting equilibrium upstream pressures recorded. As with the bubble point test, the first pores intruded at the lowest flow rates (lowest pressures) are the largest pores present in the membrane sample. Flowever, the use of two immiscible fluids with an extremely low interfacial surface tension has the advantage of requiting pressures less than 20 psi for the complete intrusion of these larger pores present in UF membranes. With knowledge of the upstream pressures corresponding to the various intrusion phase flow rates, the interfacial surface tension of the two immiscible fluids, and assuming the validity of a particular mathematical model, this test is able to calculate an effective pore size distribution of the membrane sample. Based on this entire calculated pore size distribution, the performance of conventional UF membranes was able to be correlated.

There are two major limitations associated with the disclosed technology as it pertains to rapidly and non-destructively correlating the particle retention capabilities of ultrafiltration membranes. First, the disclosed technology relies upon the generation of an entire effective pore size distribution for the tested membrane samples, an extremely tedious process which may take upwards of 2–3 hours or longer depending on the desired degree of accuracy. In addition, the two phase system disclosed by these references throughout the UF characterization experiments is an isobutanol: methanol:water (15:7:25 v/v/v) system. This solvent system may be difficult to remove from some conventional UF membranes and is toxic to most biological fluids. For these reasons, any test involving the use of this particular two phase system may render the test destructive.

It would be desirable to provide a rapid integrity test for ultrafiltration membranes which is both non-destructive and circumvents the tedious process of determining an entire effective pore size distribution for each membrane sample tested. Furthermore, it would be desirable to provide such a test which is independent of membrane surface area, porosity, and thickness; variables which can differ widely between membrane samples and often compound the difficulty in interpreting many integrity tests results. Additionally, it would be desirable to provide such a test which permits predicting with a high degree of accuracy whether a particular UF membrane is capable of retaining solutes of a given molecular size, such as biomolecules, while avoiding the need to actually challenge said membrane with a liquid solution containing the solute in order to make the determination.

SUMMARY OF THE INVENTION

The present invention is based on the discovery that, with novel modifications to the presently available permoporometric technology, a rapid and scalable non-destructive test can be developed for ultrafiltration membranes that reproducibly correlates and predicts the retention of various sized solutes, such as dextran molecules or proteins. Unlike the prior art, which relied on both the validity of a mathematical model and the measurement of numerous transmembrane pressures corresponding to stepwise increases in the intrusion phase flow rate to calculate an effective pore size distribution, the present invention relies upon the generation of only two data points to calculate a characteristic permeability ratio. Using liquid-liquid intrusion technology, a ratio of two membrane permeabilities is measured at preselected operating conditions using a pair of mutually immiscible fluids, one of which is employed as a membrane wetting agent and the other used as an intrusion fluid. The first operating condition, either a water permeability measurement or a similar measurement which can be correlated to or is proportional to the membrane permeability, is chosen such that nearly all of the membrane pores are intruded. At the second operating condition, a particular intrusion phase flow rate, is chosen so as to achieve a specified permeability ratio between the first operating condition and the second operating condition. The resulting transmembrane pressure corresponding to the intrusion phase permeability can be compared to a standard curve to predict the solute retention characteristics of the tested membrane sample.

Since a ratio of two permeability measurements is taken, the resulting value is independent of membrane surface area, porosity, tortuosity, and thickness. This is advantageous since a given ultrafiltration membrane can be configured in modules of varying size and the requirement for multiple integrity tests is eliminated. In addition, by selecting an appropriate two phase system whose constituents are both easily flushed from the membrane structure and do not adversely interact with the membrane, the developed correlative test can be rendered non-destructive. This is also advantageous since the test can then be used both pre-and post-use to validate the ultrafiltration membrane integrity.

The standard curve required to predict the solute retention capabilities of unchallenged membranes is developed in the following manner. First, a sample of the ultrafiltration membrane is challenged with a liquid solution containing non-adsorbing solute molecules of known but varying molecular size, such as dextran molecules, to determine the solute retention capabilities of the membrane. For each solute size within the liquid solution, a sieving coefficient can be calculated as the ratio of the permeate solute concentration to the feed solute concentration. The rejection coefficient for each solute size, defined as 1 minus the sieving coefficient, is then a measure of the inherent solute retention capabilities of the membrane sample. The membrane sample is then characterized by the developed liquid-liquid intrusion test by determining the transmembrane pressure required to achieve preselected permeability ratios as discussed above. Repeating this exercise with ultrafiltration membrane samples which possess similar rejection coefficients for different solute diameters, a standard curve relating the solute retention capabilities to the transmembrane pressure corresponding to a specified characteristic permeability ratio can be constructed. From this developed standard correlation, the solute retention capabilities of an unchallenged membrane sample can be predicted in a non-destructive manner solely by determining this transmembrane pressure.

DESCRIPTION OF SPECIFIC EMBODIMENTS

Figure 1:
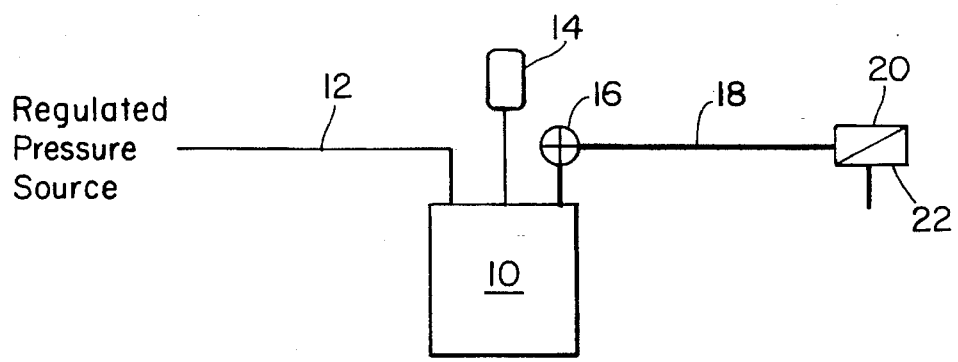
FIG. 1 is a schematic view of the apparatus utilized in Example 1 for measuring the membrane permeability ratios.

The performance of any ultrafiltration membrane is based on its ability to retain specific solutes or suspended solids. The existence of undesirably large pores within ultrafiltration membranes can drastically degrade its ability to efficiently retain solutes, such as proteins or other molecules characterized by dextrans. In addition, to completely validate the membrane process step, it is necessary to have some means of verifying pre-and post-use membrane integrity. For these reasons, it is imperative that an appropriate nondestructive test be developed which actually characterizes and quantifies the existence of these larger pores present in ultrafiltration membranes which, when present, can drastically degrade the solute retention capabilities of the membrane. Consequently, a novel scalable liquid-liquid intrusion integrity test has been developed which rapidly and non-destructively correlates and predicts the solute retention capabilities of ultrafiltration membranes. Examples of such ultrafiltration membranes include typical asymmetric membranes formed from polysulfone, polyethersulfone, regenerated cellulose, cellulose acetate, polyvinylidene difluoride, or the like, as well as composite and symmetric membranes which function as ultrafiltration membranes.

The present invention is based upon the use of novel modifications to the disclosed liquid permoporometric technique wherein a specified permeability ratio is achieved. For clarity purposes, the permeability ratio is defined as $$\frac{L_{p_1}}{L_{p_2}} = \frac{\frac{Q_1 \eta_1}{P_1}}{\frac{Q_2 \eta_2}{P_2}} \tag{2}$$

where $L_p$ is the membrane permeability, P is the transmembrane pressure resulting in a flow rate, Q, $\eta$ is the solution viscosity, and the subscripts 1 and 2 correspond to two distinct permeability measurements. From this definition, the characteristic permeability ratio is seen to consist of two distinct flow rates measured at different operating conditions and/or transmembrane pressures. A first permeability value, either a water permeability measurement or another similar measurement which is correlated to or proportional to the total membrane permeability, is chosen such that nearly all of the membrane pores are intruded. A second permeability value is established using a pair of mutually immiscible fluids, one of which is employed as a membrane wetting agent and the other as an intrusion fluid and is designed to give a specified permeability ratio. During the intrusion process, only a select number of pores are actually intruded, which varies from one membrane sample to another depending upon the actual pore size distribution of the membrane sample. The transmembrane pressure corresponding to the desired intrusion phase flow rate is determined by either (a) directly setting the intrusion phase flow rate calculated to give the desired permeability ratio and measuring the resulting transmembrane pressure (intrusion phase flow rate obtained from standard curve) or (b) carefully increasing the transmembrane pressure until the desired intrusion phase flow rate is achieved to give the specified permeability ratio (iterative procedure). The transmembrane pressure required to achieve the desired permeability ratio is then compared to a previously determined standard curve developed for the same class of membrane which correlates a solute retention characteristic, such as the molecular size of the solute rejected at a specified rejection coefficient, to the measured transmembrane pressure to determine the retention characteristics of the membrane being tested.

The standard curve is obtained by both challenging samples of similar ultrafiltration membranes with a liquid containing non-adsorbing solutes of known, but varying molecular size, such as a mixture containing various sized dextran molecules, and measuring the required transmembrane pressure necessary to achieve a specified permeability ratio in accordance with the present invention. Once the standard curve has been developed, the ability of an ultrafiltration membrane for retaining solutes, such as dextran molecules or proteins, can be determined by measuring its characteristic transmembrane pressure required to achieve a specified permeability ratio obtained from either procedure described above. The standard curve permits a direct measure of the solute retention capabilities of the tested membrane sample to be made without the need to actually challenge the ultrafiltration membrane with solutes of varying size, such as dextran molecules.

The motivation for determining a characteristic transmembrane pressure required to achieve a specified permeability ratio is twofold. First, from a theoretical standpoint, an appropriately determined ratio at a specified transmembrane pressure can be shown to be an approximate measure of the solute rejection coefficient. From theoretical arguments, the solute rejection coefficient, R, defined as one minus the sieving coefficient, can be approximated as:

$$R = 1 - C_p/C_f \approx 1 - L_{d_p}/L_{tot} \tag{3}$$

where $C_p$ and $C_f$ are the permeate and feed solute concentrations, respectively, $L_{tot}$ is the total amount of flow through the membrane sample under a given set of operating conditions (total membrane permeability), and $L_{d_p}$ represents the membrane permeability consisting only of the flow through those membrane pores equal in size or larger than $d_p$, the solute diameter. The developed liquid-liquid intrusion technology is eminently suitable for measuring this permeability ratio. From Equation 3, it is apparent that in order for two membranes to have the same rejection coefficient (for the same or differently sized solute diameters), their respective permeability ratios must be identical. Rearranging equation 1, the solute hydraulic diameter is seen to be related to the transmembrane pressure required to achieve this specified permeability ratio as:

$$d_p = \frac{4K\gamma\cos\theta}{P} \tag{4}$$

Therefore, given a desired level of solute rejection (synonymous with setting a target permeability ratio), a plot of the inverse of the solute diameter rejected at the specified level versus the transmembrane pressure required to achieve the particular permeability ratio corresponding to the specified rejection level should yield a straight line. Consequently, this methodology can be used to approximate what size solute would be expected to be rejected at a predetermined level.

Second, since a ratio of two different permeabilities is calculated, the integrity test value is essentially unaffected by differences in membrane surface area, porosity, tortuosity, and thickness. This feature allows the comparison of completely different ultrafiltration membranes on a single scale. In addition, a given ultrafiltration membrane can be configured within modules of varying size and the requirement for multiple integrity tests is eliminated.

In order to determine the transmembrane pressure corresponding to the desired permeability ratio, a two-step procedure is followed. First, the total permeability of the ultrafiltration membrane sample is determined. This can by accomplished by either a simple water permeability measurement or another similar measurement which can be correlated to or is proportional to the total membrane flux. This measurement made at this first operating condition is, in effect, a measure of the total permeability of the membrane sample and represents an approximation to $L_{tot}$ in Equation 3. Using this permeability measurement, the necessary intrusion phase flow rate required to achieve a predetermined permeability ratio can either be calculated (from the standard curve) or iteratively obtained. As stated above, this specific target permeability ratio is solely dependent upon the desired solute rejection level as shown in Equation 3. Second, the calculated intrusion phase flow rate through the membrane sample is achieved. This is accomplished by wetting the membrane sample with one of two immiscible fluids (wetting phase). The other immiscible phase (intrusion phase) is placed upstream of the membrane sample and either forced to permeate through the membrane sample at the desired intrusion phase flow rate calculated from the standard curve or forced to permeate through the membrane sample by continually increasing the intrusion phase flow rate and monitoring the transmembrane pressure until the desired permeability is achieved. In both cases, this second step can be accomplished by either setting the intrusion phase directly with a pump, for example, or by increasing the transmembrane pressure in an increasing step-wise fashion until the desired intrusion phase flow rate or permeability is achieved. After the system has been allowed to equilibrate, the resulting transmembrane pressure is measured. As shown by Equations 3 and 4, this transmembrane pressure, along with an appropriate standard curve, is then a direct non-destructive measure of the solute rejection capabilities of the tested membrane sample.

Depending upon specific requirements, many alterative methodologies can be employed for establishing correlative tests. Although all employ the concept of a permeability ratio which correlates a solute retention characteristic, subtle differences in the definition of the permeability ratio or the specific retention characteristic can alter the appearance of the correlation. However, all of these different methodologies are easily derived from the principles described above. The example will attempt to illustrate a couple of these different methodologies.

An important step in the present invention is the a priori determination of the permeability ratio required to achieve a specified solute rejection level. According to equation 3, the permeability ratio is directly related to the solute rejection coefficient. Therefore, all that is required is to set a solute rejection coefficient and calculate the theoretical permeability ratio. For example, if a solute rejection coefficient of 0.9 is desired, Equation 2 states that a permeability ratio of 0.1 should be employed. Often, a more convenient way to express this permeability ratio is by taking the logarithm of the inverse permeability ratio. In the above example, this translates into log(10), or 1. It should be noted that this approximation to the permeability ratio assumes that both the total membrane permeability and intrusion phase flow rate were measured under comparable conditions, i.e., transmembrane pressure and solution viscosity. If this is not the case, differences in these variables are appropriately normalized according to equation 2. This normalization procedure is illustrated in the example.

The two immiscible liquids which are utilized in the test should not damage or degrade the membrane so as to render the test non-destructive. That is, the liquids should not adversely affect the mechanical strength of the membrane such as would be the case where a liquid exhibits a solvent effect on the membrane. In addition, the liquids should be easily removable from the membrane or, if not completely removable, should not exhibit a toxic effect on liquid compositions to be treated with the membrane. An example of such an innocuous system is the two phase system formed upon mixing polyethylene glycol (MW 8000), ammonium sulfate, and water in a weight ratio 8:13:79. This two phase system possesses a low interfacial surface tension, a necessary property required of the two phase system in order to intrude nanometer sized pores with realistic pressures. In addition, both the polyethylene glycol and ammonium sulfate can be easily removed from the membrane with water and both are acceptable non-toxic reagents for many pharmaceutical applications. The biological acceptance of this liquid system contrasts with the methanol/isobutanol/water system of the prior art which is biologically toxic. In cases where toxicity issues are not relevant, the present invention can be performed utilizing alternative two phase liquid systems, such as those produced by mixing hexane with water, by mixing isopropyl alcohol (IPA) with an aqueous salt solution, or by utilizing any other two phase system which comprises a wetting phase and an intrusion phase.

The following example illustrates the invention and is not intended to limit the same.

EXAMPLE 1

The developed liquid-liquid intrusion integrity test was employed to correlate and predict the rejection of variously sized dextran molecules on typical polysulfone ultrafiltration membranes with differing molecular weight cutoffs, available from Millipore Corporation, Bedford, Mass. The specific two phase liquid system employed in this example consisted of the two phases formed upon the mixing of polyethylene glycol, molecular weight 8000 (PEG-8000), ammonium sulfate, and deionized water in the weight ratio 8:13:79, which was prepared and allowed to equilibrate for at least 12 hours. This two phase system was selected since both the major constituents, PEG-8000 and ammonium sulfate, are easily flushed from the polysulfone membrane and both are acceptable non-toxic reagents for pharmaceutical applications.

The system illustrated in FIG. 1 was configured to measure the liquid-liquid intrusion permeability ratios for the various tested membrane samples. As shown in FIG. 1, deionized water, e.g., the reagent used to measure the total membrane permeability, is housed within pressure dispensing vessel 10. Pressurized gas is supplied to pressure dispensing vessel 10 from a regulated and controlled pressure source (not shown) via conduit 12 and the resulting pressure measured by calibrated pressure gauge 14 located on pressure dispensing vessel 10. When valve 16 is opened, pressurized water passes through conduit 18 to membrane test cell 20 which houses the desired membrane sample to be tested. The membrane sample 22 is positioned in test cell 20 such that the skinned surface faces upstream, the normal orientation of the polysulfone ultrafiltration membrane according to standard operating protocols. The regulated source pressure (not shown) is increased until pressure as measured by calibrated pressure gauge 14 reads 20 psig, and valve 16 is opened. Membrane sample 22 positioned in test cell 20 is flushed with deionized water for 20 minutes to remove glycerin used as a standard humectant from membrane structure. The regulated pressure source is then decreased until pressure as measured by calibrated pressure gauge 14 reads 5 psig. The resulting deioinized water flow rate through membrane sample 22 is then measured gravimetrically. This measurement, along with the transmembrane pressure, represents a numerical representation of $L_{tot}$ in Equation 3.

The deionized water housed within pressure dispensing vessel 10 is replaced with the wetting liquid, e.g., the PEG-8000 rich top phase in the two phase system employed in this example. Pressurized gas is supplied to pressure dispensing vessel 10 from a regulated and controlled pressure source (not shown) via conduit 12 and the resulting pressure measured by calibrated pressure gauge 14 located on pressure dispensing vessel 10. When valve 16 is opened, pressurized wetting liquid passes through conduit 18 to membrane test cell 20 which houses the desired membrane sample to be tested. The regulated source pressure (not shown) is increased until pressure as measured by calibrated pressure gauge 14 reads 60 psig, and valve 16 is opened. Membrane sample 22 positioned in test cell 20 is flushed with wetting fluid for 40 minutes in order to complete exchange the water within the membrane pores with the wetting fluid.

The membrane wetting fluid housed within pressure dispensing vessel 10 is then replaced with the intrusion liquid, e.g., the ammonium sulfate rich bottom phase in the two phase system employed in this example. Pressurized gas is supplied to pressure dispensing vessel 10 from a regulated and controlled pressure source via conduit 12 and the resulting pressure measured by calibrated pressure gauge 14 located on pressure dispensing vessel 10. When valve 16 is opened, pressurized intrusion fluid passes through conduit 18 to membrane test cell 20 which houses the desired membrane sample to be tested. The regulated source pressure is increased until pressure, as measured by calibrated pressure gauge 14, reads 2 psig, and valve 16 is opened. The system is allowed to equilibrate for 5 minutes at which time the intrusion phase flow rate is measured gravimetrically. The source pressure is increased to 4 psid, and again the system is allowed to equilibrate for 5 minutes before measuring the equilibrium intrusion phase flow rate. The system pressure is incrementally increased and the above procedure repeated until the entire pressure range of interest is spanned. These measurements represent a numerical representations of $L_{dp}$ in Equation 3. Finally, the logarithms of the permeability ratios (LPR's) for the membrane samples at each tested pressure are calculated as $$LPR(P) = \log\left(\frac{\frac{P}{5} Q_{water}}{Q_{d_p}}\left(\frac{\eta_{water}}{\eta_{int}}\right)\right) \quad (5)$$

where P is the system pressure corresponding to the intrusion phase flow rate, $Q_{dp}$, and $Q_{water}$ is the water flow rate measured at 5 psi. $\eta_{int}$ and $\eta_{water}$ represent the solution viscosities of the intrusion phase and water, respectively. A viscosity ratio is employed in Equation 5 to correct the water flow rate and intrusion flow rate measurements for viscosity differences. In this example, the intrusion phase viscosity is approximately two times that of water. The P/5 ratio in the numerator of Equation 5 is used to correct for pressure differences between the water flow rate and intrusion flow rate measurements. The end result is the permeability ratio given by equation 5.

Figure 2:
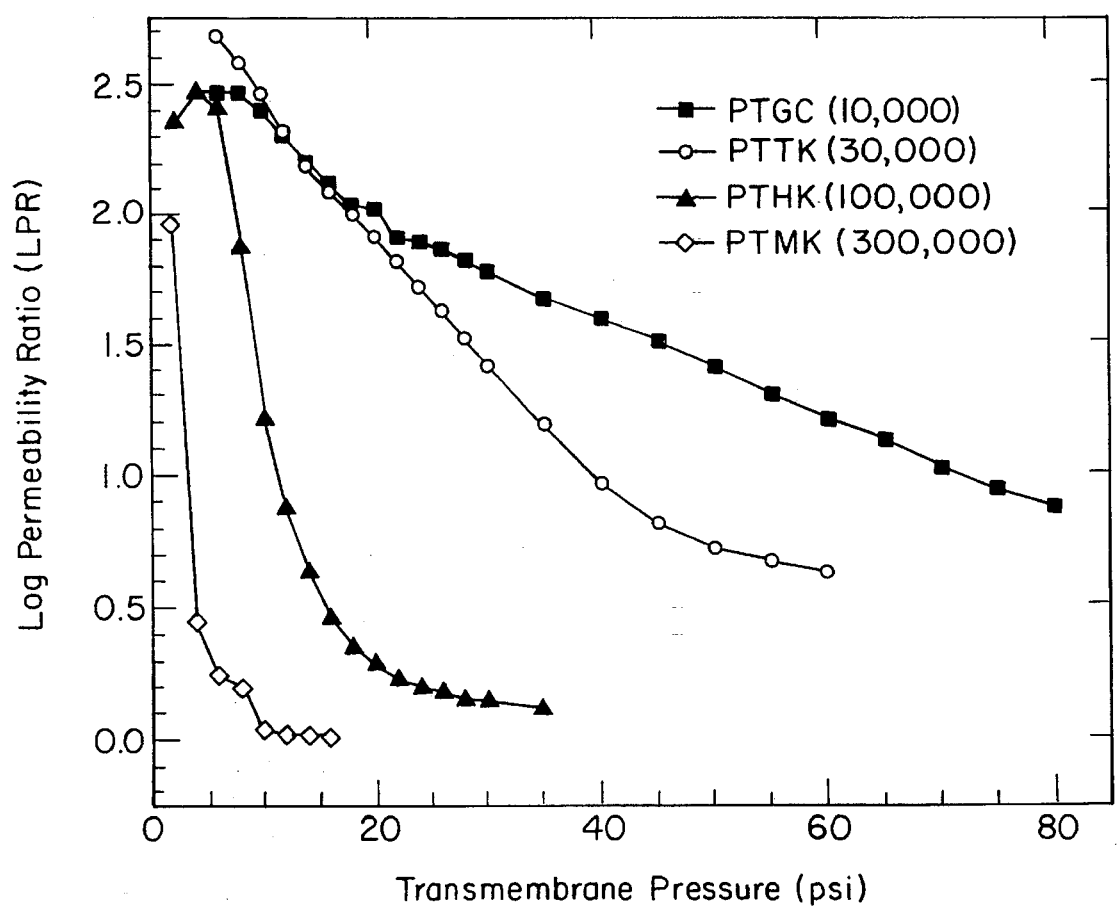
FIG. 2 are the log permeability ratios as a function of transmembrane pressure for the various tested membrane samples utilized in Example 1.

FIG. 2 illustrates the resulting LPR as a function of transmembrane pressure for polysulfone membranes with nominal molecular weight limits of 10,000, 30,000, 100, 000, and 300,000. As expected, the transmembrane pressure required to achieve a certain LPR increases with decreasing nominal molecular weight limit, indicating higher rejection coefficients of similar sized solutes. These data illustrated in FIG. 2 can be used in many distinct, yet equivalent methodologies for establishing predictive solute retention correlations. The following 3 cases, although not exhaustive, exemplify this important characteristic.

Case 1

The developed liquid-liquid intrusion integrity test was employed to correlate and predict the retention of a 4.2 nm and a 18.6 nm dextran solute on typical polysulfone ultrafiltration membranes with differing molecular weight cut-offs. In order to establish a correlation, it was first necessary to determine the appropriate transmembrane pressure required to intrude 4.2 nm and 18.6 nm diameter pores, those pores readily accessible to the 4.2 nm and 18.6 nm diameter solutes. For the PEG:ammonium sulfate:water two phase system employed in this example, the interfacial tension between the two immiscible phases lies between 0.25 and 0.3 dynes/cm. Assuming cylindrical pores with circular aperatures and a contact angle of 0, the Young/Laplace equation, given by equation 1, predicts approximate transmembrane pressures of 35 psi and 8 psi to intrude 4.2 nm and 18.6 nm diameter pores, respectively.

Figure 3:
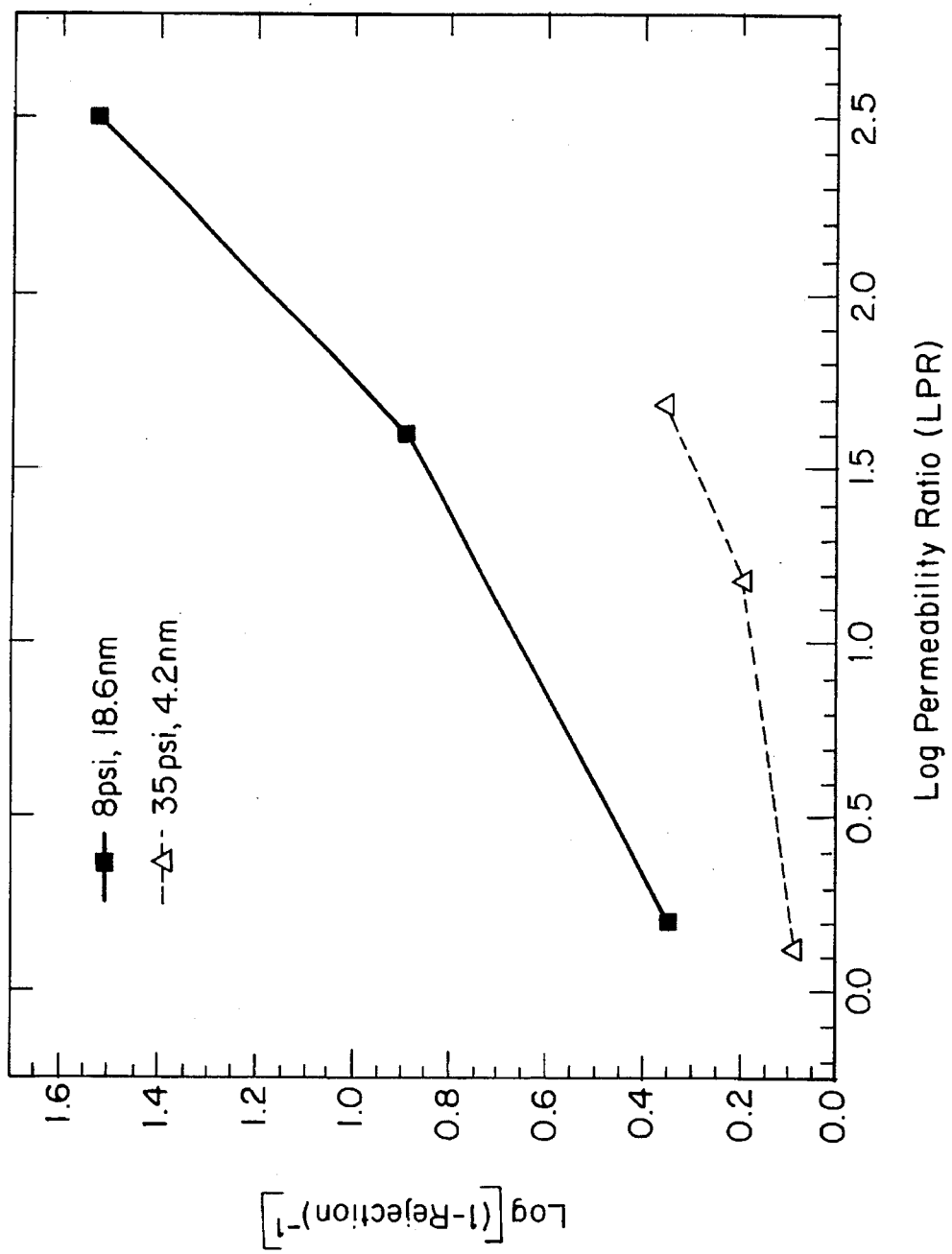
FIG. 3 is a standard curve developed in accordance with Example 1, case 1.

From the data illustrated in FIG. 2 and dextran rejection curves obtained on representative samples of 10,000, 30,000, 100,000, and 300,000 MWCO polysulfone membrane, a correlation between solute retention and LPR (logarithm of the permeability ratio) can be constructed. FIG. 3 shows the logarithm of the solute rejection coefficient as a function of membrane LPR for 4.2 nm and 18.6 nm diameter dextran solutes. These curves were generated by obtaining the LPR for each polysulfone membrane at transmembrane pressures of 8 and 35 psi (see FIG. 2) and plotting these values against the logarithm of the membrane's rejection coefficient for 18.6 nm and 4.2 nm dextran molecules. As expected from theoretical arguments and seen in FIG. 3, there is a strong correlation between the solute retention capabilities of the various membrane samples and the integrity test permeability ratios. In fact, a membrane capable of removing only 90% of solutes sized 18.6 nm in diameter is easily distinguishable from a membrane capable of removing 97% of the stone solutes.

Case 2

Figure 4:
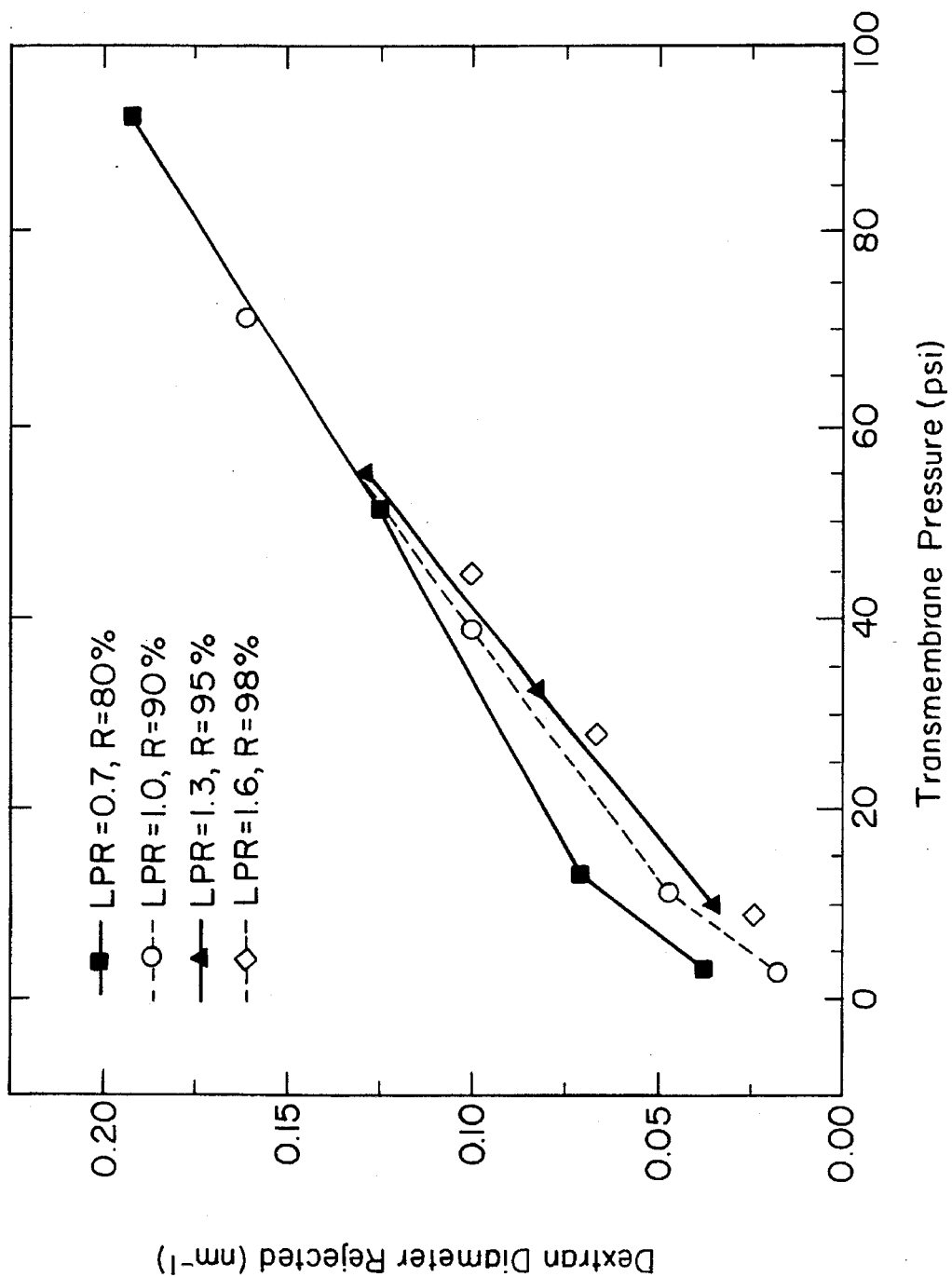
FIG. 4 is a standard curve developed in accordance with Example 1, case 2.

To establish a correlation between size of dextran solute rejected at 80%, 90%, 95%, and 98% and transmembrane pressure, it is necessary to first determine the appropriate LPR's to be employed. From Equation 3, solute rejections of 80, 90, 95, and 98% correspond to LPR's of 0.7, 1.0, 1.3, and 1.6, respectively. From the data illustrated in FIG. 2 and dextran rejection curves obtained on representative samples of 10,000, 30,000, 100,000, and 300,000 MWCO polysulfone membrane, a correlation between size of dextran solute rejected and transmembrane pressure can be established. FIG. 4 shows the inverse of the dextran hydraulic diameter rejected versus transmembrane pressure for LPR's of 0.7, 1.0, 1.3, and 1.6, corresponding to rejection coefficients of 0.8, 0.9, 0.95, and 0.98, respectively, for the various polysulfone membranes. These curves were generated by obtaining the transmembrane pressures required to achieve a certain LPR (see FIG. 2) and plotting these data against the inverse of the dextran diameter retained at the specified rejection levels for each of the tested membrane samples. Thus, each curve in FIG. 4 essentially consists of one data point from each of the various membrane samples. As expected from theoretical arguments, a strong linear relationship exists between the inverse of the dextran hydraulic diameter rejected at a specified level and the transmembrane pressure required to achieve the specified LPR. From this figure, it is readily apparent that membranes capable of rejecting dextrans molecules at 80% with a hydraulic diameter of 5 nm are easily distinguishable from membranes capable of rejecting dextran molecules at 80% with a hydraulic diameter of 7.5 nm. The developed liquid-liquid intrusion technology is obviously extremely sensitive for correlating solute retention behavior on ultrafiltration membranes.

Case 3

Figure 5:
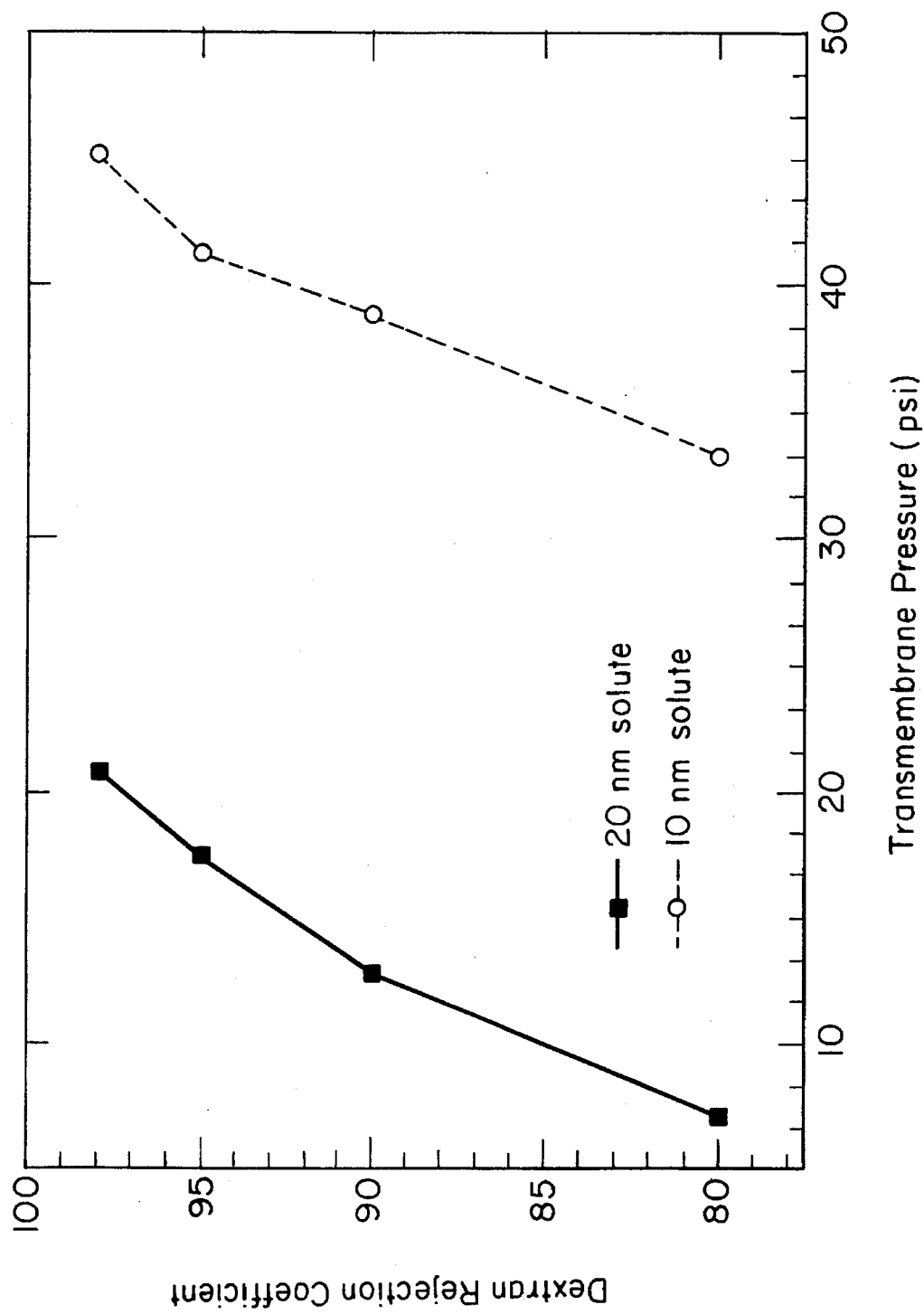
FIG. 5 is a standard curve developed in accordance with Example 1, case 3.

A correlation can also be established relating the solute rejection coefficient for a specific sized solute (theoretically shown to be related to the membrane permeability ratio) to the transmembrane pressure required to achieve the desired permeability ratio. FIG. 5 shows an alterative means for representing the data depicted in FIG. 4, where the dextran solute rejection coefficients for 10 nm and 20 nm solutes are plotted as a function of transmembrane pressure required to achieve a specific permeability ratio. As seen in FIG. 5, the transmembrane pressure required to achieve a specific permeability ratio appears to be a sensitive means for discriminating membranes based on their ability to retain specifically sized solutes. As seen in FIG. 5, a membrane capable of retaining 95% of a 20 nm dextran solute is easily distinguishable from a membrane capable of retaining only 90% of the same solute.

We claim:

1. The process for non-destructively testing an ultrafiltration membrane to determine the membrane's solute retention capabilities which comprises:

determining a standard relationship between the degree of retention of a solute having a certain molecular size by a first set of membranes with a first factor consisting of the ratio of the permeability of a first intrusion liquid through said first set of membranes wet with a wetting liquid immiscible with said intrusion liquid measured at a constant transmembrane pressure to the permeability of a second intrusion liquid through said first set of membranes measured at a constant transmembrane pressure that effects nearly complete intrusion of pores of said membrane, wetting a sample of said membrane with said wetting liquid, passing said first and second intrusion liquids at said pressures through said samples of said membrane to determine a second factor consisting of the ratio of the permeability of a said first intrusion liquid through said membrane sample wet with said wetting liquid immiscible with said intrusion liquid measured at said constant transmembrane pressure to the permeability of said second intrusion liquid through said membrane sample measured at said constant transmembrane pressure that effects nearly complete intrusion of pores of said membrane sample, comparing said second factor ratio with said standard relationship thereby to determine the degree of retention of said solutes by said sample of said membrane, said wetting fluid and said intrusion fluid being nondestructive to said membrane, and said transmembrane pressures and said transmembrane permeabilities being nondestructive to said membrane.

2. The process of claim 1 wherein said measured permeabilities are established by directly setting said transmembrane pressures.

3. The process of claim 1 wherein said permeabilities are adjusted so as to achieve said transmembrane pressures.

4. The process of any one of claims 1, 2, or 3 wherein the said first intrusion fluid and said second intrusion fluid are identical.

5. The process of any one of claims 1, 2, or 3 wherein the second intrusion liquid is water.

6. The process for non-destructively testing an ultrafiltration membrane to determine the membrane's retention capabilities of a specified sized solute which comprises:

determining a standard relationship between the degree of retention of specified sized solute by a first set of membranes with a correlating transmembrane pressure determined through a two step process which includes first, intruding said first set of membranes with a first intrusion fluid at a first transmembrane pressure to effect nearly complete intrusion of pores and measuring resulting first permeability and second, measuring the correlating transmembrane pressure required to flow a second intrusion fluid at a prescribed second permeability established to give a predetermined permeability ratio with said first permeability through said first set of membranes wet with a wetting fluid immiscible with said second intrusion fluid, intruding a sample of said membrane with said first intrusion fluid at said first transmembrane pressure to effect nearly complete intrusion of pores of said membrane and measuring first permeability wetting said sample of said membrane with said wetting fluid passing said second intrusion fluid through said sample of said membrane wet with said wetting fluid at prescribed second permeability to establish predetermined permeability ratio with said first permeability measuring the correlating transmembrane pressure required to achieve said second permeability and comparing said correlating transmembrane pressure with said standard relationship thereby to determine the solute retention capabilities by said sample of said membrane, said second intrusion fluid being immiscible with said wetting fluid, said first and second intrusion fluids and said wetting fluid being nondestructive to said membrane, and said transmembrane pressures and said transmembrane permeabilities being nondestructive to said membrane.

7. The process of claim 6 wherein said transmembrane pressures are established by directly setting said permeabilities.

8. The process of claim 6 wherein said transmembrane pressures are adjusted to as to achieve said permeabilities.

9. The process of any one of claims 6, 7, or 8 wherein the said first intrusion fluid and said second intrusion fluid are identical.

10. The process of any one of claims 6, 7, or 8 wherein the said first intrusion fluid and wetting fluid are identical.

11. The process of any one of claims 6, 7, or 8 wherein the said first intrusion fluid is water.

12. The process of any one of claims 1, 2, 3 wherein the said intrusion fluid is water rich in ammonium sulfate and lean in polyethylene glycol and is essentially equilibrated with said wetting fluid comprised of water rich with polyethylene glycol and lean in ammonium sulfate and wherein said intrusion fluid is immiscible with said wetting fluid.

13. The process of any one of claims 6, 7, or 8 wherein the said second intrusion fluid is water rich in ammonium sulfate and lean in polyethylene glycol and is essentially equilibrated with said wetting fluid comprised of water rich with polyethylene glycol and lean in ammonium sulfate and wherein said second intrusion fluid is immiscible with said wetting fluid.

14. The process of any one of claims 1,2,3, 6, 7 or 8 wherein said membrane is an ultrafiltration membrane.

15. The process of any one of claims 1,2,3, 6, 7 or 8 wherein said membrane is a symmetric membrane which functions as an ultrafiltration membrane.

16. The process of any one of claims 1, 2, 3, 6, 7, 8, 9, 10, 11, 12, or 13 wherein said membrane is a symmetric membrane which functions as an ultrafiltration membrane.

17. The process of any one of claims 1,2,3, 6, 7 or 8 wherein the solute is a dextran molecule.

18. The process of any one of claims 1,2,3, 6, 7 or 8 wherein the solute is a protein molecule.

19. The process of claim 4 wherein said membrane is an ultrafiltration membrane.

20. The process of claim 5 wherein said membrane is an ultrafiltration membrane.

21. The process of claim 4 wherein said membrane is a composite membrane which functions as an ultrafiltration membrane.

22. The process of claim 5 wherein said membrane is a composite membrane which functions as an ultrafiltration membrane.

23. The process of claim 6 wherein said membrane is an ultrafiltration membrane.

24. The process of claim 7 wherein said membrane is an ultrafiltration membrane.

25. The process of claim 8 wherein said membrane is an ultrafiltration membrane.

26. The process of claim 6 wherein said membrane is a composite membrane which functions as an ultrafiltration membrane.

27. The process of claim 7 wherein said membrane is a composite membrane which functions as an ultrafiltration membrane.

28. The process of claim 8 wherein said membrane is a composite membrane which functions as an ultrafiltration membrane.

\* \* \* \* \*

UNITED STATES PATENT AND TRADEMARK OFFICE
CERTIFICATE OF CORRECTION

PATENT NO.   : 5,457,986
DATED        : October 17, 1995
INVENTOR(S)  : Anthony J. DiLeo et al.

It is certified that error appears in the above-identified patent and that said Letters Patent is hereby corrected as shown below:

Column 10,
Line 31, replace "stone" with -- same --.

Signed and Sealed this

Thirtieth Day of September, 2003

JAMES E. ROGAN
*Director of the United States Patent and Trademark Office*